United States Patent
Kawamoto et al.

(10) Patent No.: US 11,958,799 B2
(45) Date of Patent: Apr. 16, 2024

(54) METHOD FOR PRODUCING HYDROGEN AND CARBOXYLIC ACID

(71) Applicants: Kyoto University, Kyoto (JP); Shin-Etsu Chemical Co., Ltd., Tokyo (JP)

(72) Inventors: Haruo Kawamoto, Kyoto (JP); Eiji Minami, Kyoto (JP); Yuanyuan Zhao, Kyoto (JP); Takashi Nomura, Kyoto (JP); Kazuto Kobayashi, Tokyo (JP); Akiko Miki, Tokyo (JP)

(73) Assignees: KYOTO UNIVERSITY, Kyoto (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 17/965,899

(22) Filed: Oct. 14, 2022

(65) Prior Publication Data
US 2023/0138638 A1    May 4, 2023

(30) Foreign Application Priority Data

Oct. 29, 2021  (JP) ................. 2021-177510

(51) Int. Cl.
*C01B 3/32* (2006.01)
*B01J 21/06* (2006.01)
(Continued)

(52) U.S. Cl.
CPC ............ *C07C 51/16* (2013.01); *B01J 21/063* (2013.01); *B01J 23/626* (2013.01); *C01B 3/326* (2013.01);
(Continued)

(58) Field of Classification Search
CPC ........ C07C 51/16; C07C 51/00; B01J 21/063; B01J 23/626; B01J 35/1014; B01J 37/18; B01J 37/033; C01B 3/326; C01B 2203/06; C01B 2203/1047
USPC ...................................... 423/648.1
See application file for complete search history.

(56) References Cited

U.S. PATENT DOCUMENTS

2015/0086473 A1    3/2015 Yamaguchi et al.

FOREIGN PATENT DOCUMENTS

WO    WO. 2013/125712 A1    8/2013

OTHER PUBLICATIONS

Gorbanev et al., Acetic Acid Formation by Selective Aerobic Oxidation of Aqueous Ethanol over Heterogeneous Ruthenium Catalysts, 2012, ACS Catalysis, vol. 2, pp. 604-612 (Year: 2012).*
(Continued)

*Primary Examiner* — Sheng H Davis
*Assistant Examiner* — Ritu S Shirali
(74) *Attorney, Agent, or Firm* — Birch, Stewart, Kolasch & Birch, LLP

(57) ABSTRACT

In a method for producing hydrogen and carboxylic acid, a primary alcohol of 1 to 7 carbon atoms and water are reacted by being continuously introduced into a flow reactor packed with a solid catalyst consisting of an alloy of ruthenium and tin on a support and passed through the reactor under temperature and pressure conditions at which the water assumes a gaseous state. This method enables hydrogen and carboxylic acid to be produced in a high yield or at a high purity from a primary alcohol and water in a short time and by simple operations.

6 Claims, 1 Drawing Sheet

(51) Int. Cl.
    *B01J 23/62*      (2006.01)
    *C07C 51/16*      (2006.01)
(52) U.S. Cl.
    CPC .. *C01B 2203/06* (2013.01); *C01B 2203/1047* (2013.01)

(56) References Cited

OTHER PUBLICATIONS

Wu et al., Electrooxidations of ethanol, acetaldehyde and acetic acid using PtRuSn/C catalysts prepared by modified alcohol-reduction process, 2007, Journal of Power Sources, vol. 172, pp. 180-188 (Year: 2007).*

Brei et al., "Synthesis of acetic acid from ethanol-water mixture over Cu/ZnO—ZrO2—Al2O3 catalyst" Applied Catalysis A: General, 2013, 458, 196-200.

Diagne et al., "Hydrogen production by ethanol reforming over Rh/CeO2—ZrO2 catalysts" Catalysis Communications, 2002, 3, pp. 565-571.

Kuwahara et al., " A Sustainable Method for the Synthesis of Acetic Acid Based on Dehydrogenation of an Ethanol-Water Solution Catalyzed by an Iridium Complex Bearing a Functional Bipyridonate Ligand" ChemCatChem, 2018, 10, 3636-3640.

Xiang et al., "Production of acetic acid from ethanol over CuCr catalysts via dehydrogenation-(aldehyde-water shift) reaction", RSC Adv., 2017, 7, 38586-38593.

\* cited by examiner

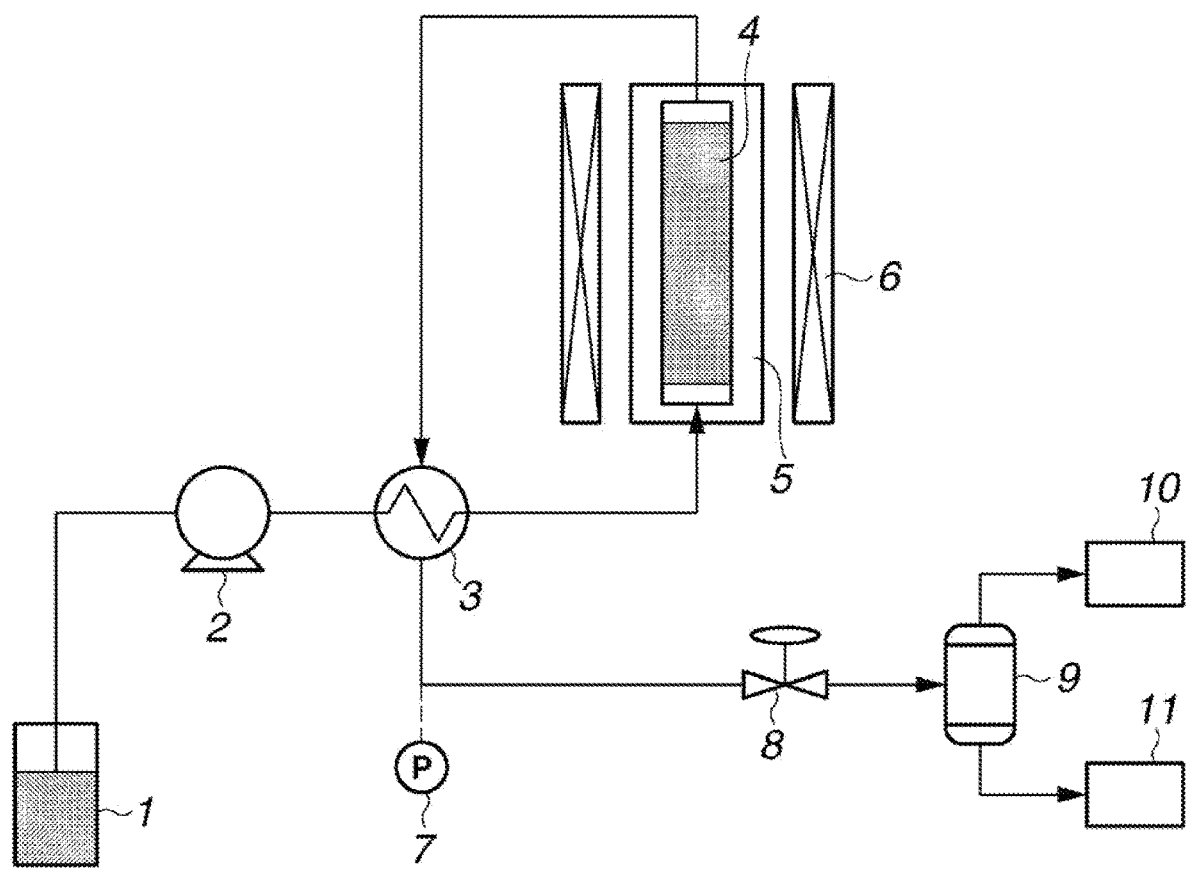

METHOD FOR PRODUCING HYDROGEN AND CARBOXYLIC ACID

CROSS-REFERENCE TO RELATED APPLICATION

This non-provisional application claims priority under 35 U.S.C. § 119(a) on Patent Application No. 2021-177510 filed in Japan on Oct. 29, 2021, the entire contents of which are hereby incorporated by reference.

TECHNICAL FIELD

The present invention relates to a method for producing hydrogen and carboxylic acid.

BACKGROUND ART

Biomass is an important resource which is expected, through use as an alternative to petroleum, natural gas and other fossil resources, to reduce dependency on such fossil resources and help limit the rise in atmospheric carbon dioxide that is a major cause of global warming. Although bioethanol produced from cellulosic biomass is used today primarily as an alternative to fossil fuels, from the standpoint of promoting the replacement of fossil resources with biomass, there is a desire for the development of methods for utilizing biomass not only as fuels but also as chemical feedstocks. One concern is that, when utilizing aqueous bioethanol solutions obtained by alcohol fermentation, there are energy outlays and costs associated with removing the water by a process such as distillation or membrane separation of the water from an azeotropic mixture. The ability to use such aqueous bioethanol solutions without having to remove the water would be desirable.

Ethanol reformation in which hydrogen is obtained from ethanol and water is a familiar technology that uses ethanol as a chemical feedstock and converts it to useful chemical substances. *Catalysis Communications* 3 (2002), pp. 565-571 reports, for example, a method that uses a Rh/CeO$_2$—ZrO$_2$ catalyst at from 400° C. to 500° C.

In ethanol reformation, by having a metal catalyst act on ethanol and water, the water works as an oxidizing agent and the ethanol is successively oxidized to acetaldehyde, acetic acid and ultimately carbon dioxide, along with which hydrogen is produced. The overall ethanol reformation reaction is represented in the manner of formula (1) below.

$$C_2H_5OH + 3H_2O \rightarrow 6H_2 + 2CO_2 \quad (1)$$

Also under study is a process which does not, as in ethanol reformation, release the carbon from ethanol as carbon dioxide, but rather, in the manner of formula (2) below, utilizes it as acetic acid, which is an intermediate of ethanol reformation. In this process, two molecules of hydrogen and one molecule of acetic acid can be obtained from one molecule of ethanol and one molecule of water.

$$C_2H_5OH + H_2O \rightarrow 2H_2 + CH_3COOH \quad (2)$$

Hydrogen, in addition to wide industrial use in applications such as petroleum refining and the manufacture of chemicals, is expected to see future growth in practical use as an energy source aimed at the realization of carbon neutrality, that is, the realization of a low-carbon society, by 2050. When hydrogen is used in fuel cells, it is essential for the hydrogen to be of high purity so that the platinum catalyst is not poisoned by carbon monoxide. The steam reformation process, which is the chief method for producing hydrogen today, uses fossil fuels such as natural gas and petroleum as the feedstock, and moreover discharges carbon dioxide. A hydrogen production process that uses recyclable resources as the feedstock and does not discharge carbon dioxide is thus desired. As for acetic acid, this is a useful chemical substance that is industrially utilized in many fields, including chemistry, food products and pharmaceuticals.

Processes in which hydrogen and a carboxylic acid are obtained from a primary alcohol and water include the processes reported in WO 2013/125712 A1 and *Chem Cat Chem*, 2018, 10, 3636-3640 for producing hydrogen and a carbonyl compound in a high yield by the dehydrogenation of an alcohol under refluxing conditions using as the catalyst an organic-iridium complex with nitrogen-containing ligands. A process for producing hydrogen and acetic acid from an aqueous ethanol solution using a flow reactor and a Cu/ZnO—ZrO$_2$—Al$_2$O$_3$ catalyst under atmospheric pressure and at 250° C. to 300° C. has also been described (*Applied Catalysis A: General* 458 (2013), 196-200). In addition, a method for producing hydrogen and acetic acid from an aqueous ethanol solution using a flow reactor and a CuCr catalyst at 623 K (350° C.) has been reported (*RSC Advances*, 2017, 7, 38586-38593).

SUMMARY OF THE INVENTION

However, in the art described in WO 2013/125712 A1 and *Chem Cat Chem*, 2018, 10, 3636-3640, when ethanol is used as the feedstock, a reaction time of at least 18 hours is required in a batch reaction, leaving room for improvement in shortening the reaction time. Also, in *Chem Cat Chem*, the reaction solution is vacuum dried, after which the catalyst is recovered by extraction with dichloromethane and concentration; hence, complex operations are required for catalyst recovery. In addition, the catalyst used is an organometallic catalyst, and so the catalyst stability and durability are concerns. Also, the raw materials for this catalyst are a complex of the precious metal iridium and special nitrogen-containing ligands, both of which are expensive. Hence, from the standpoint of use in industrial applications, there remain challenges in terms of cost.

*Applied Catalysis A: General* 458 (2013) reports that acetic acid is obtained in a maximum yield of 73.3% from an aqueous ethanol solution, and that about 2 moles of hydrogen is produced per mole of acetic acid. Hence, the hydrogen yield is presumed to be only about 150%, as opposed to the theoretical yield of 200%. Also, in *RSC Advances*, 2017, 7, 38586-38593, substantially complete conversion of ethanol is achieved using argon as the carrier gas and using an alloy consisting of 70 wt % copper and 30 wt % chromium as the catalyst, but the selectivity for acetic acid in the resulting product is only 48%. Hence, there exists a desire for further improvement in the yield of both hydrogen and acetic acid.

In *Applied Catalysis A*, even under the above conditions where the maximum value (73.3%) for the acetic acid yield was recorded, several percent of ethyl acetate, acetaldehyde, methyl ethyl ketone and butanol formed as by-products. In *RSC Advances*, the acetaldehyde in the product obtained under these conditions rises to about 50%. In light of this, further improvement is also desired in the purity of the liquid to be produced. Additionally, the reaction is carried out at a high temperature of 250° C. to 300° C. in *Applied Catalysis A*, and at a high temperature of 350° C. in *RSC Advances*. When this reaction is industrially utilized, given that a lower reaction temperature enables the product to be obtained using less energy and is thus preferred, there is also a desire for further improvement in terms of the reaction temperature.

It is therefore an object of this invention to provide a method for the production of hydrogen and carboxylic acid which produces hydrogen and a carboxylic acid in a high yield from a primary alcohol and water in a short time and by way of simple operations. It is also an object of this invention to provide a method for the production of hydrogen and carboxylic acid which produces hydrogen and a carboxylic acid at a high purity from a primary alcohol and water in a short time and by way of simple operations.

We have found that by carrying out the reaction in a flow reactor using a solid catalyst consisting of an alloy of ruthenium and tin on a support, hydrogen and carboxylic acid can be obtained in a high yield from a primary alcohol and water, or hydrogen and carboxylic acid can be obtained at a high purity from a primary alcohol and water.

Accordingly, the invention provides a method for producing hydrogen and carboxylic acid, which method includes the step of reacting the primary alcohol of 1 to 7 carbon atoms with water by continuously introducing a primary alcohol of 1 to 7 carbon atoms and water into a flow reactor packed with a solid catalyst consisting of an alloy of ruthenium and tin (Ru—Sn alloy) on a support and passing the alcohol and water through the flow reactor under temperature and pressure conditions at which the water assumes a gaseous state.

In a preferred embodiment of the production method of the invention, the flow reactor has therein a temperature of between 185° C. and 350° C. and a pressure of from 0.1 to 15 MPa.

In another preferred embodiment, the Ru—Sn alloy has a ruthenium content of from 25 to 200 parts by weight per 100 parts by weight of tin.

In yet another preferred embodiment, the primary alcohol is ethanol and acetic acid is produced as the carboxylic acid.

In still another preferred embodiment, the primary alcohol of 1 to 7 carbon atoms and water introduced to the flow reactor have a residence time therein of not more than 60 seconds.

In a further preferred embodiment, the solid catalyst is composed of particles of a Ru—Sn alloy-supporting metal oxide or carbonaceous material.

ADVANTAGEOUS EFFECTS OF THE INVENTION

The method of the invention is able to shorten the residence time, i.e., the reaction time, of a primary alcohol of 1 to 7 carbon atoms and water introduced as the feedstock to a flow reactor packed with a solid catalyst to 60 seconds or less, and enables hydrogen and a carboxylic acid of 1 to 7 carbon atoms to be obtained in high yield or high purity by way of simple operations. The solid catalyst consisting of an alloy of ruthenium and tin on a support is an inorganic catalyst and thus has excellent stability and durability, in addition to which reuse is easy.

BRIEF DESCRIPTION OF THE DIAGRAMS

FIG. 1 is a schematic diagram showing an example of the construction of a flow-type reaction system such as may be used in the inventive method for producing hydrogen and carboxylic acid.

DESCRIPTION OF THE EMBODIMENTS

[Method for Producing Hydrogen and Carboxylic Acid]

The inventive method for producing hydrogen and carboxylic acid is a production process in which a feedstock composed of a primary alcohol of 1 to 7 carbon atoms and water is subjected to a dehydrogenation reaction in a flow reactor (column). The process is characterized by continuously introducing a primary alcohol of 1 to 7 carbon atoms and water to a flow reactor packed with a solid catalyst consisting of an alloy of ruthenium and tin (Ru—Sn alloy) on a support, passing the alcohol and water through the flow reactor under temperature and pressure conditions at which the water assumes a gaseous state, and reacting the alcohol with the water. The phase state of the primary alcohol of 1 to 7 carbons and water when introduced into the flow reactor packed with solid catalyst may be any of the following: a liquid state, a gaseous state, or a liquid and gaseous state (i.e., a gas-liquid mixed state).

Feedstock

This invention uses a primary alcohol and water as the feedstock.

The number of carbon atoms on the primary alcohol is from 1 to 7, and preferably from 1 to 3. Because the reaction is carried out by bringing an aqueous solution of the primary alcohol into contact with the solid catalyst, the primary alcohol is not particularly limited so long as it is soluble in water. Specific examples include linear saturated aliphatic primary alcohols such as methanol, ethanol, 1-propanol, 1-butanol and 2-pentanol; branched saturated aliphatic primary alcohols such as isobutyl alcohol and isopentyl alcohol; unsaturated aliphatic primary alcohols such as allyl alcohol; and aromatic primary alcohols such as benzyl alcohol. One of these may be used alone or two or more may be used in combination. Of these, ethanol is preferred because it can be produced from biomass employed to reduce dependency on fossil resources and limit the rise of carbon dioxide. The ethanol is not particularly limited, provided that it is industrially available at a certain degree of high purity (such as an impurity level, aside from water, of not more than 3%). Either synthetic ethanol or fermentation ethanol (also known as "bioethanol" or "biomass ethanol") may be used. When ethanol is used as the feedstock, acetic acid is produced as the carboxylic acid in this invention.

The water is water that is free of impurities such as ions and organic matter. Pure water such as distilled water, deionized water or purified water is preferred.

The primary alcohol and water, when introduced into the solid catalyst-packed flow reactor, may be in either a liquid state or a gaseous state. That is, the primary alcohol and water may be vaporized at the interior of the flow reactor or may be vaporized prior to introduction into the flow reactor.

In cases where the primary alcohol and water are introduced to the solid catalyst-packed flow reactor in a liquid state, the primary alcohol and water are mixed together and introduced to the interior of the flow reactor. The timing of mixture of the primary alcohol and water is not particularly limited; an aqueous solution of the primary alcohol obtained by prior mixture may be passed through the flow reactor, or the primary alcohol and water may be mixed just before entering the flow reactor or at the interior of the flow reactor prior to being brought into contact with the solid catalyst.

In cases where the primary alcohol and water are to be introduced to the solid catalyst-packed flow reactor in a gaseous state, an empty column may be inserted into the system just prior to the flow reactor inlet, the temperature and pressure may be set so that the water assumes a gaseous state at the interior of the empty column, and either the feedstock introduced to the empty column may be in the form of a premixed aqueous solution of the primary alcohol or the primary alcohol and water may be introduced separately to the column. Alternatively, the primary alcohol and water may be introduced to the flow reactor in a gaseous state obtained by vaporization using a known method other than the foregoing method that employs an empty column.

At the interior of the flow reactor, the primary alcohol and water in a gaseous state are brought into contact with the solid catalyst and reacted.

The molar amount of water per mole of the primary alcohol as the feedstock is preferably from 1 to 25,000 moles, more preferably from 2.5 to 5,000 moles, and even more preferably for 20 to 2,500 moles. For example, in cases where the feedstock is passed through the reactor as an aqueous solution of primary alcohol, in order to obtain the desired product in a high yield, the concentration of the primary alcohol in the aqueous solution is preferably from 0.1 to 700 g/L, more preferably from 0.5 to 500 g/L, and even more preferably from 1 to 100 g/L.

Flow Reactor

The flow reactor is a flow-type reaction vessel in the form of a column that is incorporated into the subsequently described flow-type reaction system. This reaction vessel is packed at the interior with a solid catalyst consisting of an alloy of ruthenium and tin on a support, and is designed in such a way that the primary alcohol and water (aqueous solution of primary alcohol) introduced as the feedstock passes through the interior in a vaporized state while coming into contact with the solid catalyst and the resulting reaction product can be discharged.

Solid Catalyst

The solid catalyst used in this invention is a catalyst for reacting the primary alcohol of 1 to 7 carbon atoms with water. It consists of an alloy of ruthenium and tin (Ru—Sn alloy) on a support.

The material making up the support is not particularly limited, provided that it can support the Ru—Sn alloy and does not adversely affect the reaction between the primary alcohol of 1 to 7 carbons and water. Exemplary supports include metal oxides such as titanium dioxide ($TiO_2$), silica ($SiO_2$) and alumina ($Al_2O_3$), and carbonaceous materials such as activated carbon, carbon black and graphite. Given that the catalyst is expected to act as a Lewis acid catalyst, titanium dioxide is preferred. Any one of these materials by itself, or combinations of two or more thereof, may be used as the material making up the support.

The ruthenium content in the Ru—Sn alloy, from the standpoint of producing hydrogen and carboxylic acid in a high yield from the primary alcohol and water, is preferably from 25 to 200 parts by weight, more preferably from 50 to 150 parts by weight, and even more preferably from 90 to 110 parts by weight, per 100 parts by weight of tin.

The content of uncombined tin in the solid catalyst is not particularly limited. For example, in cases where titanium dioxide particles are used as the support, from the standpoint of suppressing by-products in the reaction between the primary alcohol of 1 to 7 carbons and the water and thereby increasing the hydrogen purity and raising the carboxylic acid yield, the tin content per 100 parts by weight of the support is preferably from 1 to 20 parts by weight, and more preferably from 1 to 10 parts by weight.

The shape of the solid catalyst, i.e., the shape of the carrier, is not particularly limited. However, taking into consideration the ability to pack the catalyst into the flow reactor and the fact that a larger surface area of contact with the feedstock is better for catalyst function, the catalyst is preferably granular. Therefore, it is especially preferable for the solid catalyst to be composed of particles made of Ru—Sn alloy supported on the above metal oxide or carbonaceous material. The support may be prepared by an alkoxide process or the like as subsequently described, or a prepared reagent or other commercially available powder may be used directly as is.

Here, in cases where the support is granular, a solid catalyst in the form of a powder that has passed through a sieve having openings of preferably from 30 to 180 μm, more preferably from 40 to 130 μm, and even more preferably from 50 to 90 μm, is desirable. A smaller screen aperture is more preferable because the particle size of the solid catalyst is smaller, resulting in a larger surface area of contact with the feedstock.

The specific surface area of the support, although not particularly limited, is preferably from 30 to 1,000 m²/g, and more preferably from 50 to 300 m²/g. A larger specific surface area is more preferable because the surface area of contact between the solid catalyst and the feedstock becomes larger. The specific surface area refers here to the value determined by the nitrogen adsorption method.

The solid catalyst used in the invention may be prepared by a method known to the art.

The method for supporting the alloy of ruthenium and tin is not particularly limited; a known method may be used for this purpose. However, from the standpoint of dispersing the ruthenium and tin, placing them on a support and increasing the activity of the solid catalyst, a coprecipitation method is preferred. Coprecipitation is a method in which the precipitation of poorly soluble salts is achieved by adding a precipitant to a metal salt solution containing a plurality of target metals. For example, by adding a base as the precipitant to an aqueous solution of a plurality of metal salts, the precipitation of metal hydroxides that are poorly soluble salts can be achieved. In a case where one wishes to place a poorly soluble salt on a support, the support should be made present within the metal salt solution. The alloy can be obtained by achieving precipitation of the poorly soluble salt, rinsing and drying where necessary, subsequently firing to form the metal oxide, and additionally reducing with hydrogen or the like.

The solid catalyst used in this invention may be prepared by Method (1) or (2) below.

Method (1) for Preparing Solid Catalyst:

This method for preparing the solid catalyst used in the invention includes the steps of:

(i) forming a precipitate containing at least one metal selected from titanium, silicon and aluminum by adding an alkoxide solution of at least one alkoxide selected from alkoxides of titanium, silicon and aluminum to an aqueous solution containing (a) ruthenium ions and (b) tin ions;

(ii) coprecipitating components (a) and (b) by further adding a precipitant; and (iii) obtaining a solid catalyst consisting of a Ru—Sn alloy on a support by separating off and removing the precipitate obtained in step (ii) via filtration, centrifugal separation or the like, heating and drying the precipitate, subsequently baking the dried precipitate in an oxygen-containing atmosphere at between 300° C. and 1,000° C., and then carrying out reducing treatment in a reducing atmosphere at between 300° C. and 800° C.

Here, the raw material for component (a) is not particularly limited, so long as it is a compound which yields ruthenium ions and dissolves in a solvent. Examples include ruthenium compounds such as ruthenium chloride, ruthenium nitrate and ruthenium nitrosyl nitrate. These may be used singly or two or more may be used in combination.

Based on availability and cost considerations, ruthenium chloride ($RuCl_3 \cdot nH_2O$) is preferred. The purity is preferably at least 95 wt %, and more preferably at least 97 wt %.

The raw material for component (b) is not particularly limited, so long as it is a compound which yields tin ions and dissolves in a solvent. Examples include tin compounds such as tin chloride, tin sulfate, sodium stannate and tin acetate. These may be used singly or two or more may be used in combination. Based on availability and cost considerations, tin chloride ($SnCl_2 \cdot 2H_2O$) is preferred. The purity is preferably at least 95 wt %, and more preferably at least 97 wt %.

These raw materials are each weighed out in amounts corresponding to the composition of the Ru—Sn alloy that is to be ultimately produced and the amount that is to be supported, and are dissolved in a solvent (a neutral or acidic aqueous solution). That is, the raw material for component (a) and the raw material for component (b) are each weighed out so as to achieve the intended composition as an Ru—Sn alloy and in the amounts to be supported.

Dissolution of the raw materials for components (a) and (b) that have been weighed out may be effected by mixing together these raw materials and then dissolving the mixed powder in a solvent (a neutral or acidic aqueous solution) or by successive dissolution of the respective raw materials.

The solvent used is not particularly limited, so long as it dissolves the raw materials for components (a) and (b) without forming complex ions with the raw materials and is capable of including ions of components (a) and (b). Examples include pure water, 5N aqueous nitric acid, aqueous sulfuric acid and aqueous hydrochloric acid. Of these, pure water is preferred.

The alkoxide solution of at least one alkoxide selected from alkoxides of titanium, silicon and aluminum is a solution of at least one alkoxide selected from titanium, silicon and aluminum alkoxides (metal alkoxides) dissolved in an alcohol or other organic solvent.

The at least one type of alkoxide selected from titanium, silicon and aluminum alkoxides (metal alkoxides) is a compound in which at least one metal selected from titanium, silicon and aluminum (preferably titanium, silicon or aluminum) is bonded to an alkoxide group, and should be a compound in which the hydrogen on the hydroxyl group of an alcohol has been substituted with at least one metal selected from titanium, silicon and aluminum (preferably titanium, silicon or aluminum). The specific structure is not particularly limited, although an alkoxide of the formula $M(OR)_n$ (wherein M is titanium, silicon or aluminum; OR is a single alkoxy group or differing alkoxy groups (R being an alkyl group of 1 to 4 carbons), and n is an integer from 2 to 4) is preferred.

Preferred examples of alcohols as the organic solvent include ethanol, methanol, butanol, 2-propanol and ethoxyethanol. Ethanol, methanol and 2-propanol are more preferred.

In Step (i) of Method (1) for preparing the solid catalyst, when an alkoxide solution of at least one alkoxide selected from those of titanium, silicon and aluminum is added to an aqueous solution containing (a) ruthenium ions and (b) tin ions, the metal alkoxide included in the alkoxide solution undergoes a hydrolytic condensation reaction, forming a precipitate that includes at least one metal selected from titanium, silicon and aluminum (a sol and/or gel-like precipitate made of a polymer alkoxide or colloidal polymer containing metal-oxygen-metal bonds from the metal alkoxide).

The precipitant used in Step (ii) of Method (1) for preparing the solid catalyst is not particularly limited, so long as it raises the pH of the aqueous solution containing components (a) and (b) and induces precipitation of the poorly soluble salt. Examples include sodium hydroxide, potassium hydroxide, sodium carbonate, ammonia and urea. These may be used singly, a plurality may be used in combination, or they may be prepared as an aqueous solution and added.

In Step (ii) of Method (1) for preparing the solid catalyst, there is no particular limitation on the method of adding a precipitant (base) to the aqueous solution containing components (a) and (b) following formation of a precipitate containing at least one metal selected from titanium, silicon and aluminum and thereby precipitating (coprecipitating) components (a) and (b) as poorly soluble salts. For example, the precipitant may be added to an aqueous solution containing components (a) and (b) while the solution is held at between 10° C. and 35° C. and stirred. Following addition of the precipitant, in order to bring precipitation (coprecipitation) to completion, it is desirable to leave the solution to stand at rest and allow it to age. The aging temperature is preferably between 10° C. and 35° C., and the aging time is preferably from 1 to 24 hours.

In Step (iii) of Method (1) for preparing the solid catalyst, the precipitate obtained in Step (ii) is separated off and removed by filtration, centrifugal separation or the like, and then heated and dried, following which the dried precipitate is baked in an oxygen-containing atmosphere at between 300° C. and 1,000° C. This method may involve, for example, placing the heated and dried precipitate within an oven and heating it under a stream of air. The baking temperature is preferably between 300° C. and 1,000° C., and more preferably between 350° C. and 600° C. The baking time is preferably from 0.5 to 5 hours. In this case, the Ru—Sn mixed oxide is supported on particles made of at least one type of metal oxide selected from oxides of titanium, silicon and aluminum.

Next, the Ru—Sn mixed oxide obtained by baking is subjected to reducing treatment at between 300° C. and 800° C. This method may involve heating the metal oxide under a stream of hydrogen. The reducing temperature is preferably between 300° C. and 800° C., and more preferably between 350° C. and 500° C. The reducing time is preferably from 1 to 10 hours.

A solid catalyst consisting of metal oxide particles of at least one type of metal selected from titanium, silicon and aluminum that support a Ru—Sn alloy can be obtained in this way.

Method (2) for Preparing Solid Catalyst:

This method for preparing the solid catalyst used in the invention includes the steps of:

(ii') adding particles composed of at least one metal oxide selected from titanium, silicon and aluminum oxides or a carbonaceous material to an aqueous solution containing (a) ruthenium ions and (b) tin ions, and then coprecipitating components (a) and (b) by adding a precipitant;

(iii') obtaining a solid catalyst consisting of a Ru—Sn alloy on a support by separating off and removing the precipitate obtained in step (ii') via filtration, centrifugal separation or the like, heating and drying, subsequently baking the dried precipitate in an oxygen-containing atmosphere at between 300° C. and 1,000° C., and then carrying out reducing treatment in a reducing atmosphere at between 300° C. and 800° C.

The particles used here may be the same as described above. That is, it is desirable to use particles which are composed of a metal oxide such as titanium dioxide, silica or alumina or a carbonaceous material such as activated carbon, carbon black or graphite, and which have passed through a sieve having openings of preferably from 30 to 180 μm, more preferably from 40 to 130 μm, and even more preferably from 50 to 90 μm, and which have a specific surface area of from 30 to 1,000 m$^2$/g, and more preferably from 50 to 300 m$^2$/g.

The method and conditions in Step (ii') of Method (2) for preparing a solid catalyst may be the same as those in Step (ii) of Method (1) for preparing a solid catalyst.

The method and conditions in Step (iii') of Method (2) for preparing a solid catalyst may be the same as those in Step (iii) of Method (1) for preparing a solid catalyst.

A solid catalyst composed of particles of a metal oxide such as titanium dioxide, silica or alumina, or a carbonaceous material such as activated carbon, carbon black or graphite that support a Ru—Sn alloy can be obtained in this way.

In the inventive method for producing hydrogen and carboxylic acid, it is essential to set the temperature and pressure conditions at the interior of the flow reactor in such a way that the water assumes a gaseous state.

Here, the pressure at the interior of the flow reactor, that is, the pressure when the primary alcohol and water introduced as the feedstock are brought into contact with the solid catalyst, is a pressure at which water assumes a gaseous state at the subsequently described temperature. From the standpoint of producing the reaction product in a high yield, the pressure is preferably from 0.1 to 20 MPa, more preferably from 0.1 to 18 MPa, even more preferably from 0.1 to 15 MPa, and most preferably from 0.1 to 10 MPa. From the standpoint of producing the reaction product in a high purity, the pressure is preferably from 0.1 to 20 MPa, more preferably from 0.1 to 10 MPa, even more preferably from 0.2 to 6 MPa, and most preferably from 0.5 to 4 MPa.

The temperature at the interior of the flow reactor, that is, the temperature when the primary alcohol and water introduced as the feedstock are brought into contact with the solid catalyst, in order to produce the reaction product in a high yield, is at or above the temperature at which water assumes a gaseous state under the above pressure, i.e., at or above the boiling point of water at the above pressure. The boiling point of water is, for example, 312° C. at a pressure of 10 MPa, 297° C. at 8.2 MPa, 276° C. at 6 MPa, 251° C. at 4 MPa, 212° C. at 2 MPa, 152° C. at 0.5 MPa. and 100° C. at 0.1 MPa. When the temperature is too high, the intermediate which is an aldehyde or the carboxylic acid obtained as the product decomposes, forming carbon monoxide or carbon dioxide, methane and the like. Therefore, the preferred range in temperature at the interior of the flow reactor varies according to the pressure, being from 312 to 340° C. when the pressure is 10 MPa, from 297 to 340° C. when the pressure is 8.2 MPa, from 276 to 320° C. when the pressure is 6 MPa, from 251 to 320° C. when the pressure is 4 MPa, from 212 to 300° C. when the pressure is 2 MPa, from 152 to 290° C. when the pressure is 0.5 MPa. and from 100 to 280° C. when the pressure is 0.1 MPa. The boiling point of water at various pressures can be determined with the steady state process simulator Pro/II, version 10.1 (Schneider Electric).

From the above, the temperature and pressure conditions at the interior of the flow reactor are the temperature and pressure at which water assumes a gaseous state. To produce the reaction product in a high yield, it is preferable for the temperature to be between 200° C. and 350° C. and the pressure to be between 0.1 and 15 MPa, and more preferable for the temperature to be between 251° C. and 340° C. and the pressure to be between 0.1 and 10 MPa. To produce the reaction product at a high purity, it is preferable for the temperature to be between 185° C. and 300° C. and the pressure to be between 0.1 and 4 MPa. and more preferable for the temperature to be between 185° C. and 250° C. and the pressure to be between 0.1 and 2 MPa.

The residence time t (seconds) of the reaction solution, i.e., the primary alcohol and water that are introduced as the feedstock, at the interior of the flow reactor (catalyst packed section) refers to the reaction time, and is expressed by formula (3) below.

$$t=\phi V/(F\rho/\rho')\times 60 \quad (3)$$

In the formula, $\phi$ is the void fraction at the flow reactor interior (catalyst packed section), V is the volume (mL) of the flow reactor interior (catalyst packed section), F is the flow rate (mL/min) at standard atmospheric temperature and pressure (SATP), $\rho$ is the density (g/cm$^3$) of the reaction solution at SATP, and $\rho'$ is the density (g/cm$^3$) of the reaction solution under the reaction conditions (temperature and pressure at interior of flow reactor).

The densities $\rho$ and $\rho'$ can be estimated from the Soave-Redlich-Kwong model using the steady state process simulator Pro/II, version 10.1 (Schneider Electric).

The residence time t, from the standpoint of suppressing the formation of carbon dioxide and methane due to decomposition of the intermediate which is an aldehyde or the carboxylic acid obtained as the product, is preferably not more than 60 seconds, more preferably from 0.03 to 30 seconds, even more preferably from 0.04 to 20 seconds, and still more preferably from 0.05 to 10 seconds.

By suitably adjusting the flow rate of the reaction solution under standard atmospheric temperature and pressure (SATP) and the inside diameter and length at the flow reactor interior (catalyst packed section), it is possible to set the residence time t to the desired time.

The inventive method for producing hydrogen and carboxylic acid is carried out using a flow-type reaction system wherein the feedstock (reaction solution) is continuously introduced to a high-temperature high-pressure environment and from which the reaction product is discharged. The reaction system is not particularly limited provided that it is a flow-type reaction apparatus capable of continuously passing the feedstock (reaction solution) through a flow reactor packed with a solid catalyst at a given temperature and pressure. A known apparatus of this type may be used for this purpose.

For example, a flow-type reactor system like that shown in FIG. 1 may be used in the inventive method for producing hydrogen and carboxylic acid.

The system shown in FIG. 1 has a feedstock tank 1 which holds a primary alcohol of 1 to 7 carbons and water (here, an aqueous solution of the primary alcohol), a flow reactor (column) 4 packed with a solid catalyst consisting of a Ru—Sn alloy on a support, a high-pressure pump 2 which delivers the primary alcohol of 1 to 7 carbons and water within the feedstock tank 1 to the flow reactor 4, a heat exchanger 3 which carries out heat exchange between the primary alcohol of 1 to 7 carbons and water within the feedstock tank 1 and the mixture following reaction (reaction product) from the flow reactor 4, an aluminum block 5 for heat shielding, an electric furnace 6 for heating the flow reactor 4, a pressure gauge 7, a back-pressure value 8, a gas/liquid separator 9, a gas recovery section 10 such as a gas bag, and a liquid recovery section 11 such as a glass bottle.

The high-pressure pump 2 has an intake side that is connected by a fluid distribution line to the feedstock tank 1 containing the primary alcohol of 1 to 7 carbons and water (aqueous solution of primary alcohol) so as to be enable liquid transfer, and a discharge side that is connected by a fluid distribution line to the inlet side of the flow reactor 4 via the heat exchanger 3. The pump 2 is a high-pressure delivery pump capable of discharging at high pressure the primary alcohol of 1 to 7 carbons and water (aqueous solution of primary alcohol) serving as the feedstock.

The flow reactor 4 is a vessel of, for example, cylindrical shape having at either end in the lengthwise direction an inlet for introducing the primary alcohol of 1 to 7 carbons and water (aqueous solution of primary alcohol) serving as the feedstock and an outlet for discharging the reaction product. The vessel is packed at the interior with a solid catalyst consisting of a Ru—Sn alloy on a support in such a way as to have a degree of voids that allows the primary alcohol of 1 to 7 carbons and water (aqueous solution of primary alcohol) introduced as the feedstock to vaporize and pass therethrough. The interior of the flow reactor 4 is also referred to herein as the "catalyst packed section."

The discharge side of the flow reactor 4 is connected by flow distribution lines to the gas-liquid separator 9 via the heat exchanger 3 and the back-pressure valve 8 in such manner as to enable the reaction product discharged from the flow reactor 4 to pass therethrough. The gas-liquid separator 9 carries out gas-liquid separation of the reaction product that has been discharged from the flow reactor 4 and cooled by the heat exchanger 3. The gas-liquid separator 9 has a gas discharge section that is connected to a gas recovery section (gas bag) 10, and a liquid discharge section that is connected to a liquid recovery section (glass bottle) 11.

The pressure gauge 7 measures the pressure in the system from the high-pressure pump 2 to the back-pressure valve 8. Based on the pressure measurement results, the pressure of delivery by the high-pressure pump 2 and the pressure of release from the back-pressure valve 8 are adjusted so as to set the interior of the flow reactor 4 to the desired pressure mentioned above.

In addition, the interior of the flow reactor 4 is heated by the electric furnace 6 and adjusted to the above-mentioned temperature.

Hydrogen and carboxylic acid are produced as follows in the flow reaction system shown in FIG. 1.

First, a primary alcohol of 1 to 7 carbons and water (aqueous solution of primary alcohol) are continuously introduced to the flow reactor 4 from the feedstock tank 1. At this time, the primary alcohol of 1 to 7 carbons and water (aqueous solution of primary alcohol) delivered from the high-pressure pump 2 are heated to a given degree by the heat exchanger, rendering them into a readily vaporizable state, and are introduced to the flow reactor 4.

Next, because the interior of the flow reactor 4 has been set to a temperature and pressure at which water assumes a gaseous state, the primary alcohol of 1 to 7 carbons and water (aqueous solution of primary alcohol) that have been introduced vaporize and pass through the interior of the flow reactor 4 while contacting the solid catalyst.

At this time, when the primary alcohol of 1 to 7 carbons and water (aqueous solution of primary alcohol) comes into contact with the solid catalyst, the primary alcohol of 1 to 7 carbons and the water react, forming a mixture (reaction product) that contains hydrogen and a carboxylic acid of 1 to 7 carbons.

The mixture (reaction product) that has formed is discharged from the flow reactor 4 and cooled by the heat exchanger 3, following which it is gas-liquid separated by the gas-liquid separator 9. The separated gas is hydrogen and is recovered in the gas recovery section (gas bag) 10, and the separated liquid is primarily carboxylic acid and is recovered in the liquid recovery section (glass bottle).

The construction shown in FIG. 1 is for a case in which the primary alcohol and water are introduced to the flow reactor 4 in a liquid state. In a case where the primary alcohol and water are to be introduced to the flow reactor 4 in a gaseous state, this may be accomplished by inserting an empty column into the system at a point prior to the flow reactor 4 inlet, setting the interior of the empty column to a temperature and pressure at which the water assumes a gaseous state (e.g., the same temperature and pressure as at the interior of the flow reactor 4), vaporizing the primary alcohol and water by introducing them into this column, and then introducing the vaporized primary alcohol and water to the flow reactor 4.

Following use in reacting the primary alcohol with water, the solid catalyst packed into the flow reactor 4 can be repeatedly reused after passing water therethrough to rinse the catalyst. Because it is possible to rinse the solid catalyst while in place within the flow reactor 4, there is no need for a solid catalyst recovery operation. In cases where the solid catalyst packed into the flow reactor 4 is to be reused, it is desirable to check for retention of the catalytic activity by carrying out the reaction under fixed conditions as a test. When the catalytic activity has diminished, the solid catalyst may be removed from the flow reactor 4 and regenerated by heat treatment in a hydrogen atmosphere.

As noted above, with the inventive method for producing hydrogen and carboxylic acid, the residence time (reaction time) in the flow reactor (catalyst packed section) can be shortened to 60 seconds or less, and hydrogen and a carboxylic acid of 1 to 7 carbons can be easily obtained in a high yield or at a high purity from the primary alcohol of 1 to 7 carbons and water serving as the feedstock. As used herein, "high yield" means that the yield of products recovered as liquids other than the carboxylic acid is preferably not more than 9%, more preferably not more than 5.5%, even more preferably less than 5%, and still more preferably less than 2%. Also, "high purity" means that the purity of hydrogen in the recovered gas product is preferably at least 95 mol %, more preferably at least 98 mol %, and even more preferably at least 98.5 mol %.

EXAMPLES

The following Examples and Comparative Examples are provided to illustrate the invention, but are not intended to limit the scope thereof.

Quantitative determinations of the reaction product were carried out by the following methods.

Determination of Acetic Acid, Acetaldehyde and Ethanol

Acetic acid, acetaldehyde and ethanol were quantitatively determined by high-performance liquid chromatography under the following conditions.

Apparatus: High-performance liquid chromatograph (Prominence, from Shimadzu Corporation)

Column: Aminex HPX-87H from Bio-Rad Laboratories, Inc. (inside diameter, 7.8 mm; length, 300 mm)

Mobile phase: 5 mmol/L aqueous sulfuric acid solution

Flow rate: 0.6 mL/min
Column temperature: 45° C.
Detector: Differential refractive index detector (RID-20A, from Shimadzu Corporation)
Determination of Hydrogen, $CH_4$, CO, $CO_2$, $C_2H_2$ and $C_2H_6$
Hydrogen, $CH_4$, CO, $CO_2$, $C_2H_2$ and $C_2H_5$ were quantitatively determined by gas chromatography.
Apparatus: Gas chromatograph
(CP-4900 Micro GC, from Varian Medical Systems, Inc.)
Column: CP-Molsieve 5 Å; inside diameter, 0.32 mm; length, 10 mm; membrane thickness, 0.12 µm
Carrier gas: Argon
Column inlet pressure: 170 kPa
Column temperature: 100° C.
Detector: Thermal conductivity detector
Internal standard: neon (Imamura Sanso Corporation; purity>99.999%)

Preparation of Solid Catalyst (Titanium Dioxide-Supported Ruthenium-Tin Catalyst)

Ruthenium(III) chloride (Tokyo Chemical Industry; purity, >97%; 0.821 g) and tin(II) chloride dihydrate (Nacalai Tesque Inc.; purity, >97%; 0.76 g) were dissolved in 100 mL of 60° C. distilled water, giving an aqueous solution.

While holding this aqueous solution at 60° C. and stirring, a mixture of titanium(IV) isopropoxide (Nacalai Tesque, Inc.; purity, >95%; 37.2 mL) and 2-propanol (Nacalai Tesque, Inc.; purity, >99%; 20 mL) was added dropwise over 7 minutes. The mixture was additionally stirred for 30 minutes at 25° C., whereupon a precipitate formed.

Next, 100 mL of a 0.1475 mol/L aqueous solution of sodium hydroxide was added, following which the mixture was stirred at 25° C. for 30 minutes and then left at rest for 12 hours at 25° C.

The precipitate that formed was recovered by centrifugal separation, repeatedly suspended and washed with 100 mL distilled water a total of five times, and then dried 12 hours in an oven set to 105° C.

The tin(II) chloride dihydrate and the titanium(IV) isopropoxide were used in amounts such that the weight of uncombined tin per 100 parts by weight of the titanium dioxide that forms becomes 4 parts by weight. The ruthenium(III) chloride was used in an amount such that the weight of uncombined ruthenium per 100 parts by weight of uncombined tin becomes 100 parts by weight.

Next, the precipitate was placed on a quartz boat and baked in a glass tube for 1 hour at 450° C. while having 100 mL/min of air passed therethrough, after which the precipitate was reduced for 5 hours at 400° C. while having 100 mL/min of hydrogen (purity, >99.9%) passed therethrough.

Last of all, the precipitate was passed through a sieve having 75 µm openings, giving a titanium dioxide-supported ruthenium-tin catalyst (Ru—Sn/$TiO_2$ catalyst).

The specific surface area of the resulting catalyst was 80±5 $m^2$/g. The specific surface area was determined by the nitrogen adsorption method using the Gemini VII 2390 surface area analyzer from Micromeritics Instruments Corporation.

Example 1

Hydrogen and acetic acid were produced using the flow reaction system shown in FIG. 1.

In the flow reaction system in FIG. 1, a Phoenix Flow Reactor™ from ThalesNano Inc. was used as the high-pressure pump 2, heat exchanger 3, flow reactor (column) 4, aluminum block 5, electric furnace 6, pressure gauge 7 and back-pressure valve 8, and a self-built separator was used as the gas-liquid separator 9. The flow reactor (column) 4 was packed with 0.8±0.05 g of the titanium dioxide-supported ruthenium-tin catalyst prepared as described above. The flow reactor (column) 4 interior (catalyst packed section) was cylindrical with an inside diameter of 3.9 mm and a length of 100 mm, and had a void fraction, as measured by filling it with water, of 0.66.

A 10 g/L aqueous ethanol solution placed in the feedstock tank 1 was delivered by the high-pressure pump 2 at a flow rate of 0.3 mL/min, and introduced to the flow reactor (column) 4 which was heated to 320° C. by the electric furnace 6. The aqueous ethanol solution was liquid until introduced into the flow reactor (column) 4. That is, at the time of introduction to the flow reactor (column) 4, the ethanol and water were in a liquid phase. The pressure within the system from the high-pressure pump 2 to the back-pressure valve 8 (i.e., the pressure within the flow reactor (column) 4) was maintained at 10 MPa.

The mixture following the reaction was cooled to 25° C. by the heat exchanger 3, the pressure was returned to normal pressure at the back-pressure valve 8, and gas-liquid separation was carried out by the gas-liquid separator 9, with the gas being recovered in the gas recovery section (gas bag) 10 and the liquid being recovered in the liquid recovery section (glass bottle). The gas was recovered for 10 minutes, the liquid was recovered for 5 minutes, and the product yield (% (mol/mol)) with respect to the ethanol (mol) introduced into the flow reactor (column) 4 was determined from the yields in moles of the respective substances (ingredients) present in the gas and in the liquid. The hydrogen purity was determined from the yield in moles of the respective substances (ingredients) present in the recovered gas. The recovered liquid was analyzed by high-performance liquid chromatography, as a result of which the presence of substances other than ethanol, acetic acid and acetaldehyde was not confirmed. Also, the recovered gas was analyzed by gas chromatography, as a result of which the presence of substances (ingredients) other than hydrogen, $CH_4$, CO, $CO_2$, $C_2H_4$ and $C_2H_6$ was not confirmed.

The residence time of the reaction solution in the catalyst packed section of the flow reactor (column) 4, as calculated by formula (3) above, was 8.23 seconds. The densities ρ and ρ' in formula (3) were estimated from the Soave-Redlich-Kwong model using the steady state process simulator Pro/II, version 10.1 (Schneider Electric). The results are shown in Table 1.

Example 2

Aside from setting the internal pressure from the high-pressure pump 2 to the back-pressure valve 8 to 6 MPa, the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 3

Aside from setting the internal pressure from the high-pressure pump 2 to the back-pressure valve 8 to 6 MPa and setting the temperature of the flow reactor (column) 4 to 300° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 4

Aside from setting the internal pressure from the high-pressure pump 2 to the back-pressure valve 8 to 6 MPa and setting the temperature of the flow reactor (column) 4 to 280° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 5

Aside from setting the internal pressure from the high-pressure pump 2 to the back-pressure valve 8 to 4 MPa and setting the temperature of the flow reactor (column) 4 to 260° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 6

Aside from setting the internal pressure from the high-pressure pump 2 to the back-pressure valve 8 to 2.5 MPa and setting the temperature of the flow reactor (column) 4 to 240° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 7

Aside from setting the internal pressure from the high-pressure pump 2 to the back-pressure valve 8 to 0.5 MPa and setting the temperature of the flow reactor (column) 4 to 260° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 8

Aside from setting the internal pressure from the high-pressure pump 2 to the back-pressure valve 8 to 4 MPa and setting the temperature of the flow reactor (column) 4 to 260° C., and also inserting an empty column before the inlet to the flow reactor (column) 4, setting the temperature at the interior of the empty column to 260° C. and rendering the ethanol and water at the time of introduction to the flow reactor (column) 4 into a gaseous state, the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 9

Aside from setting the internal pressure from the high-pressure pump 2 to the back-pressure valve 8 to 2 MPa, the same operations were carried out as in Example 8 and the yield (% (mob/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 10

Aside from setting the internal pressure from the high-pressure pump 2 to the back-pressure valve 8 to 0.5 MPa, the same operations were carried out as in Example 8 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 11

Aside from setting the internal pressure from the high-pressure pump 2 to the back-pressure valve 8 to 0.1 MPa, the same operations were carried out as in Example 8 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 12

Aside from setting the internal pressure from the high-pressure pump 2 to the back-pressure valve 8 to 0.1 MPa and setting the temperature of the flow reactor (column) 4 to 240° C., and also inserting an empty column before the inlet to the flow reactor (column) 4, setting the temperature at the interior of the empty column to 240° C. and rendering the ethanol and water at the time of introduction to the flow reactor (column) 4 into a gaseous state, the same operations were carried out as in Example 8 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 13

Aside from using a 100 g/L aqueous ethanol solution as the feedstock, the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 14

Aside from setting the internal pressure from the high-pressure pump 2 to the back-pressure valve 8 to 0.1 MPa and setting the temperature of the flow reactor (column) 4 to 190° C., and also inserting an empty column before the inlet to the flow reactor (column) 4, setting the temperature at the interior of the empty column to 190° C. and rendering the ethanol and water at the time of introduction to the flow reactor (column) 4 into a gaseous phase, the same operations were carried out as in Example 8 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 15

Aside from setting the internal pressure from the high-pressure pump 2 to the back-pressure valve 8 to 0.7 MPa and setting the temperature of the flow reactor (column) 4 to 190° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 16

Aside from setting the internal pressure from the high-pressure pump 2 to the back-pressure valve 8 to 1.2 MPa and setting the temperature of the flow reactor (column) 4 to 200° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Example 17

Aside from setting the internal pressure from the high-pressure pump 2 to the back-pressure valve 8 to 2 MPa and setting the temperature of the flow reactor (column) 4 to 220° C., the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Comparative Example 1

Aside from setting the temperature of the flow reactor (column) 4 to the 300° C. at which water assumes a liquid state under a pressure of 10 MPa, the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Comparative Example 2

Aside from setting the temperature of the flow reactor (column) 4 to the 280° C. at which water assumes a liquid state under a pressure of 10 MPa, the same operations were carried out as in Example 1 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

Comparative Example 3

Aside from setting the temperature of the flow reactor (column) 4 to the 260° C. at which water becomes a liquid phase under a pressure of 6 MPa, and also inserting an empty column before the inlet to the flow reactor (column) 4 and setting the temperature at the interior of the empty column to 260° C., the same operations were carried out as in Example 8 and the yield (% (mol/mol)) of the product with respect to the ethanol introduced into the flow reactor (column) 4 was determined. The results are shown in Table 1. The recovered liquid was analyzed, as a result of which the formation of substances other than those shown in Table 1 was not confirmed.

In the Examples and Comparative Examples, the same solid catalyst was rinsed with water and repeatedly used. When the solid catalyst was to be reused, the retention of catalytic activity was checked by carrying out the reaction under fixed conditions. As a result, it was possible to confirm that the same catalyst can be used for a total of 60 hours or more. Moreover, when the catalytic activity decreased, it was possible to easily regenerate the solid catalyst by heat treatment in a hydrogen atmosphere.

TABLE 1

| | | State of feedstock | Flow reactor (column) conditions | | | | Yield (% (mol/mol)) (based on ethanol introduced to column) | |
|---|---|---|---|---|---|---|---|---|
| | | When to flow reactor (column) | Pressure (MPa) | Temp. (° C.) | State of water at time of reaction | Residence time (sec) | Liquid ingredients recovered | |
| | | | | | | | Acetic acid | Ethanol |
| Example | 1 | liquid phase | 10 | 320 | gas phase | 8.23 | 67.7 | 1.7 |
| | 2 | liquid phase | 6 | 320 | gas phase | 4.08 | 75.1 | — |

TABLE 1-continued

|  |  |  |  |  |  |  |  |  |
|---|---|---|---|---|---|---|---|---|
|  | 3 | liquid phase | 6 | 300 | gas phase | 4.37 | 76.6 | 9.0 |
|  | 4 | liquid phase | 6 | 280 | gas phase | 4.76 | 60.8 | 34.3 |
|  | 5 | liquid phase | 4 | 260 | gas phase | 3.07 | 59.7 | 35.4 |
|  | 6 | liquid phase | 2.5 | 240 | gas phase | 1.88 | 48.8 | 46.8 |
|  | 7 | liquid phase | 0.5 | 260 | gas phase | 0.33 | 72.5 | 11.6 |
|  | 8 | gas phase | 4 | 260 | gas phase | 3.07 | 71.9 | 23.8 |
|  | 9 | gas phase | 2 | 260 | gas phase | 1.39 | 71.9 | 19.2 |
|  | 10 | gas phase | 0.5 | 260 | gas phase | 0.33 | 74.2 | 8.9 |
|  | 11 | gas phase | 0.1 | 260 | gas phase | 0.06 | 71.2 | 7.2 |
|  | 12 | gas phase | 0.1 | 240 | gas phase | 0.07 | 59.0 | 22.7 |
|  | 13 | liquid phase | 10 | 320 | gas phase | 8.39 | 50.7 | 37.2 |
|  | 14 | gas phase | 0.1 | 190 | gas phase | 0.07 | 16.0 | 77.6 |
|  | 15 | liquid phase | 0.7 | 190 | gas phase | 0.54 | 14.2 | 84.5 |
|  | 16 | liquid phase | 1.2 | 200 | gas phase | 0.93 | 18.2 | 81.1 |
|  | 17 | liquid phase | 2 | 220 | gas phase | 1.55 | 31.4 | 65.9 |
| Comparative Example | 1 | liquid phase | 10 | 300 | liquid phase | 110.35 | 46.7 | 42.1 |
|  | 2 | liquid phase | 10 | 280 | liquid phase | 119.44 | 21.6 | 75.4 |
|  | 3 | liquid phase | 6 | 260 | liquid phase | 92.57 | 22.2 | 76.9 |

|  |  | Yield (% (mol/mol)) (based on ethanol introduced to column) | | | | | | Purity (mol %) (in gaseous ingredients recovered) |
|---|---|---|---|---|---|---|---|---|
|  |  | Liquid ingredients recovered | Gaseous ingredients recovered | | | | | |
|  |  | Acetaldehyde | Hydrogen | $CH_4$ | CO | $CO_2$ | $C_2H_4$ | $C_2H_6$ | Hydrogen |
| Example | 1 | — | 211.3 | 40.66 | 0.07 | 31.57 | — | 0.13 | 74.5 |
|  | 2 | — | 220.0 | 36.02 | 0.04 | 30.30 | — | 0.11 | 76.8 |
|  | 3 | 0.8 | 235.4 | 23.65 | 0.22 | 17.03 | 0.02 | 0.06 | 85.2 |
|  | 4 | 0.5 | 155.6 | 9.39 | 0.06 | 6.10 | — | 0.06 | 90.9 |
|  | 5 | 0.3 | 155.0 | 5.75 | 0.03 | 3.36 | — | 0.03 | 94.4 |
|  | 6 | 0.3 | 138.6 | 3.57 | — | 2.18 | 0.01 | 0.02 | 96.0 |
|  | 7 | 4.5 | 208.6 | 15.17 | 9.45 | 4.37 | 0.16 | 0.03 | 87.7 |
|  | 8 | 0.4 | 176.8 | 7.75 | 0.06 | 4.99 | 0.01 | 0.09 | 93.2 |
|  | 9 | 1.7 | 182.4 | 9.02 | 1.64 | 5.29 | 0.04 | 0.02 | 91.9 |
|  | 10 | 3.5 | 199.4 | 15.24 | 9.92 | 4.47 | 0.15 | 0.02 | 87.0 |
|  | 11 | 5.1 | 198.7 | 18.68 | 14.53 | 4.18 | 0.25 | 0.02 | 84.1 |
|  | 12 | 8.3 | 164.8 | 8.82 | 7.63 | 1.47 | 0.11 | 0.01 | 90.1 |
|  | 13 | 2.4 | 144.6 | 10.89 | 1.18 | 7.23 | 0.02 | 0.14 | 88.1 |
|  | 14 | 4.6 | 46.4 | 0.41 | 0.38 | 0.21 | — | — | 97.9 |
|  | 15 | 0.4 | 34.8 | 0.20 | — | 0.12 | — | — | 99.1 |
|  | 16 | — | 51.3 | 0.25 | — | 0.17 | — | — | 99.2 |
|  | 17 | — | 88.4 | 0.64 | — | 0.52 | — | 0.01 | 98.7 |
| Comparative Example | 1 | 0.6 | 151.6 | 16.12 | 0.08 | 10.57 | — | 0.21 | 84.9 |
|  | 2 | 0.3 | 55.9 | 3.70 | 0.01 | 2.31 | — | 0.10 | 90.1 |
|  | 3 | 0.2 | 49.6 | 2.17 | 0.01 | 1.15 | 0.00 | 0.04 | 93.6 |

* In the table, "—" means not detected.

The above results show that when the reaction was carried out under temperature and pressure conditions at which water assumes a gaseous state and at a temperature of at least 240° C. (that is, in cases where the temperature of the flow reactor (column) 4 was set to 240° C. or more) using a solid catalyst consisting of a Ru—Sn alloy on a support, it was possible to obtain hydrogen and a carboxylic acid in a high yield from a primary alcohol and water. Also, in cases where the reaction was carried out at a temperature of at least 190° C. and not more than 220° C. (i.e., in cases where the temperature of the flow reactor (column) 4 was set to at least 190° C. and not more than 220° C.), it was possible to obtain hydrogen and a carboxylic acid at a high purity from a primary alcohol and water. Moreover, it was possible to obtain the product in a short time, i.e., a residence time in the flow reactor (catalyst packed section) of 10 seconds or less.

Also, the solid catalyst used in this invention had an excellent stability and durability, and could be easily reused by merely rinsing it with water.

Japanese Patent Application No. 2021-177510 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for producing hydrogen and carboxylic acid, comprising a step of reacting a primary alcohol of 1 to 7 carbon atoms with water by continuously introducing the primary alcohol of 1 to 7 carbon atoms and water into a flow reactor packed with a solid catalyst consisting of an alloy of ruthenium and tin on a support and passing the primary alcohol of 1 to 7 carbon atoms and water through the flow reactor under temperature and pressure conditions at which the water assumes a gaseous state.

2. The production method of claim 1, wherein the flow reactor has therein a temperature of between 185° C. and 350° C. and a pressure of from 0.1 to 15 MPa.

3. The production method of claim 1, wherein the alloy of ruthenium and tin has a ruthenium content of from 25 to 200 parts by weight per 100 parts by weight of tin.

4. The production method of claim 1, wherein the primary alcohol of 1 to 7 carbon atoms is ethanol and acetic acid is produced as the carboxylic acid.

5. The production method of claim 1, wherein the primary alcohol of 1 to 7 carbon atoms and water introduced to the flow reactor have a residence time therein of not more than 60 seconds.

6. The production method of claim 1, wherein the solid catalyst is composed of particles of the alloy of ruthenium and tin supported on a metal oxide or carbonaceous material.

\* \* \* \* \*